(12) United States Patent
Zhou

(10) Patent No.: US 10,952,835 B2
(45) Date of Patent: Mar. 23, 2021

(54) INTRA-PELVIC FUNDUS VESICAE SUPPORT AND METHOD FOR IMPLANTING SAME

(71) Applicant: Liaoning Weng Ling Medical Technology Co., Ltd., Liaoning (CN)

(72) Inventor: Jian Zhou, Liaoning (CN)

(73) Assignee: Liaoning Weng Ling Medical Technology Co., Ltd., Liaoning (CN)

(*) Notice: Subject to any disclaimer, the term of this patent is extended or adjusted under 35 U.S.C. 154(b) by 89 days.

(21) Appl. No.: 16/304,088

(22) PCT Filed: May 25, 2017

(86) PCT No.: PCT/CN2017/085812
§ 371 (c)(1),
(2) Date: Nov. 21, 2018

(87) PCT Pub. No.: WO2017/206783
PCT Pub. Date: Dec. 7, 2017

(65) Prior Publication Data
US 2019/0358013 A1    Nov. 28, 2019

(30) Foreign Application Priority Data
May 30, 2016   (CN) .......................... 201610365490.4

(51) Int. Cl.
*A61F 2/00*     (2006.01)
*A61M 31/00*   (2006.01)
(Continued)

(52) U.S. Cl.
CPC ............ *A61F 2/0022* (2013.01); *A61B 6/025* (2013.01); *A61M 31/00* (2013.01); *A61N 1/0514* (2013.01);
(Continued)

(58) Field of Classification Search
CPC ............ A61F 2/0022; A61F 2220/0008; A61F 2999/00; A61F 2/00; A61F 2240/004;
(Continued)

(56) References Cited

U.S. PATENT DOCUMENTS 4,888,022 A * 12/1989 Huebsch ............... A61F 2/4637
623/23.19
5,785,640 A    7/1998 Kresch et al.
(Continued)

FOREIGN PATENT DOCUMENTS

CN          1646067 A    7/2005
CN        101268970 A    9/2008
(Continued)

*Primary Examiner* — Navin Natnithithadha
*Assistant Examiner* — Sunita Reddy
(74) *Attorney, Agent, or Firm* — Novick, Kim & Lee, PLLC; Allen Xue

(57) ABSTRACT

An external intra-pelvic fundus vesicae support disposed at the outer fundus vesicae position and fixing the front end to the pelvic pecten pubis position to lift internal organs. An injection channel is provided inside an external intra-pelvic fundus vesicae support structure, and a screw hole is formed at an input hole, so that the support can be connected to an in-vitro device. According to the external intra-pelvic fundus vesicae support, a tomoscan three-dimensional modeling technology is used to generate a model file which completely conforms to physiological shapes of the pelvic pecten pubis and the outer fundus vesicae and the spatial form of the abdominal cavity of a typical person, and the external intra-pelvic fundus vesicae support of a frame structure and medical material quality is obtained using 3-D printing technologies. Before a surgery is conducted, a virtual reality technology is used to simulate and verify a surgical safety scheme.

7 Claims, 3 Drawing Sheets

(51) Int. Cl.
*A61B 6/02* (2006.01)
*A61N 1/05* (2006.01)
*B33Y 80/00* (2015.01)
*B33Y 50/02* (2015.01)
*B29C 64/393* (2017.01)
*G16H 50/30* (2018.01)
*G16H 20/40* (2018.01)
*B29L 31/00* (2006.01)

(52) U.S. Cl.
CPC .......... *B29C 64/393* (2017.08); *B33Y 50/02* (2014.12); *B33Y 80/00* (2014.12); *G16H 20/40* (2018.01); *G16H 50/30* (2018.01); *A61F 2220/0008* (2013.01); *A61F 2220/0041* (2013.01); *A61F 2240/004* (2013.01); *A61M 2205/3613* (2013.01); *A61M 2207/00* (2013.01); *A61M 2207/10* (2013.01); *A61M 2210/1085* (2013.01); *B29L 2031/753* (2013.01)

(58) Field of Classification Search
CPC .......... A61F 2220/0041; A61F 2/0004; G05B 19/4099; B29L 2031/753; A61M 2210/1085; A61M 31/00; A61M 2207/10; A61M 2207/00; A61M 2205/3613; B22F 5/10; B22F 3/1055; B22F 2999/00; B33Y 50/02; B33Y 80/00; B33Y 50/00; B29C 64/393; G16H 50/30; G16H 20/40; G16H 50/50; A61N 1/0514; A61B 6/025; G06F 30/00; G06F 2999/00
USPC ............................................... 600/37, 29–31
See application file for complete search history.

(56) References Cited

U.S. PATENT DOCUMENTS

| | | | | |
|---|---|---|---|---|
| 2002/0062060 A1* | 5/2002 | Gross | ................ | A61N 1/36007 600/30 |
| 2003/0216814 A1* | 11/2003 | Siegel | ................ | A61F 2/0045 623/23.66 |
| 2004/0116774 A1 | 6/2004 | Migliari | | |
| 2004/0193228 A1* | 9/2004 | Gerber | ................ | A61N 1/36071 607/39 |
| 2005/0234291 A1* | 10/2005 | Gingras | ................ | A61F 2/0063 600/30 |
| 2005/0250978 A1* | 11/2005 | Kammerer | ................ | A61F 2/0045 600/29 |
| 2006/0004421 A1* | 1/2006 | Bennett | ................ | A61N 1/37252 607/41 |
| 2007/0055095 A1* | 3/2007 | Chu | ................ | A61F 2/0045 600/37 |
| 2007/0100388 A1* | 5/2007 | Gerber | ................ | A61N 1/36007 607/41 |
| 2008/0021263 A1* | 1/2008 | Escude | ................ | A61F 2/0045 600/29 |
| 2008/0269548 A1* | 10/2008 | Vecchiotti | ................ | A61F 2/0045 600/30 |
| 2009/0054950 A1* | 2/2009 | Stephens | ................ | A61N 1/36153 607/41 |
| 2009/0247817 A1* | 10/2009 | Forsell | ................ | A61N 1/36514 600/31 |
| 2010/0081866 A1* | 4/2010 | Goddard | ................ | A61F 2/0045 600/37 |
| 2010/0130814 A1* | 5/2010 | Dubernard | ................ | A61B 17/06109 600/30 |
| 2010/0179620 A1* | 7/2010 | Wariar | ................ | A61N 1/325 607/68 |
| 2011/0257470 A1* | 10/2011 | Yi | ................ | A61F 2/0045 600/30 |
| 2013/0053688 A1* | 2/2013 | Watschke | ................ | A61N 1/0521 600/424 |
| 2013/0072998 A1* | 3/2013 | Su | ................ | A61B 5/04882 607/41 |
| 2013/0138135 A1* | 5/2013 | Rosen | ................ | A61B 17/12 606/197 |
| 2014/0221733 A1* | 8/2014 | Alexander | ................ | A61F 2/0063 600/30 |
| 2015/0025308 A1 | 1/2015 | Boden et al. | | |
| 2015/0265387 A1* | 9/2015 | Alexander | ................ | A61B 17/3468 600/37 |
| 2015/0305846 A1* | 10/2015 | Alexander | ................ | A61F 2/0045 600/30 |
| 2015/0305847 A1* | 10/2015 | Roll | ................ | A61F 2/0063 600/30 |
| 2015/0351917 A1* | 12/2015 | Link | ................ | A61F 2/32 623/22.11 |
| 2017/0049547 A1* | 2/2017 | Knipfer | ................ | A61F 2/0009 |

FOREIGN PATENT DOCUMENTS

| | | |
|---|---|---|
| CN | 102438547 A | 5/2012 |
| CN | 104981220 A | 10/2015 |
| CN | 206080765 U | 4/2017 |
| CN | 105012048 B | 2/2018 |
| EP | 0700669 A1 | 3/1996 |
| WO | 2008013867 A1 | 1/2008 |
| WO | 2008152628 A1 | 12/2008 |
| WO | 2009126476 A1 | 10/2009 |

* cited by examiner

US 10,952,835 B2

INTRA-PELVIC FUNDUS VESICAE SUPPORT AND METHOD FOR IMPLANTING SAME

TECHNICAL FIELD

The present invention discloses an external intra-pelvic fundus vesicae support implanted through a surgery. The support is used to improve the degradation of physiology and functions caused by lowering of internal organs of the body due to insufficiency of internal qi. The support relates to the fields of human senile diseases, physiological internal qi theory and medical record of traditional Chinese medicine, physiological anatomy and surgical support implantation technology in western medicine, and medical three-dimensional printing technology. It is known that "insufficiency of splenogastric qi causes lowering of internal organs of the body" in the physiology theory of the traditional Chinese medicine. Insufficiency of splenogastric qi in one's life often occurs in the old age after the age of 50, and is a life stage that everyone cannot avoid. "Splenogastric qi" is one of taxonomic definitions of physiology of traditional Chinese medicine of "internal qi". Qi in middle burner does not just mean qi of the spleen and stomach. "Qi" of "internal qi" is written by ancients as: qi, which is different from qi of five cereals, indicating that substances at the life level of qi objectively exist in human life (indicated with "qi" below) and is used for the overall process of human life. The source of internal qi is called primordial qi, i.e., qi of the former heaven. Primordial qi is life fuel given by the nature when a life of a feature originates. The quality and quantity of primordial qi is determined from the moment when life exists, and becomes exhausted with the growth of age. Insufficiency of splenogastric qi is a quantitative change stage before exhaustion of primordial qi. To this end, people in the ancient have the method of preserving primordial qi by engorging acquired qi through qi of strengthening the spleen and stomach, i.e. "vegetarian diet, deficiency of food and no cold food". A classical proven recipe "Recipe of Invigorating Spleen-Stomach and Replenishing Qi" is also used to adjust insufficiency of splenogastric qi. Qi invigorated by the "Recipe of Invigorating Spleen-Stomach and Replenishing Qi" is qi of the latter heaven, not qi of the former heaven. There are essential differences between Qi of the latter heaven and qi of the former heaven. Invigorated qi of the latter heaven can only relatively prevent consumed of the latter heaven qi from consuming qi of the former heaven, and cannot completely replace and supplement the consumed qi of the former heaven. Qi of the latter heaven from the medicine is temporarily enough after long-term taking and progressive increase of dosage under the regular action of half-life of the medicine. However, it is an objective fact that splenogastric qi in human life is bound to run out, and there are incurable periods of pain with the rest of the life. The visceral organs drop caused by insufficiency of splenogastric qi. Organ tissue and functions are damaged due to extrusion of the visceral organs inside and outside the peritoneum under the prevention of pelvic cavity and urogenital diaphragm, and the cluster of lesions in a non-isolated state occurs (see FIG. 1).

The present invention relates to known physical anatomy of western medicine, which fails to recognize the objective existence of "qi", a living substance, in human life in theory. Therefore, even though the presentational cluster of lesions, when separately characterized, has the definition of senile syndrome, the presentational cluster of lesions can only be classified according to anatomy and treated. Blood stasis caused by blocked blood circulation of the visceral organs is classified as local inflammation. Directional visceral organs gangrene due to targeted drug. Damage of side effects may be caused due to broad-spectrum drugs. Dysfunction cannot be avoided after drugs are applied to necrotic tissue excised by the surgery. This indicates that its science has defects, and the basic theory has errors, causing diagnosis and treatment errors.

The present invention relates to a known surgical implantation technology and method for an internal support of the body in western medicine. Because western medical community does not correctly recognize the cluster of lesions in lowering of visceral organs in the abdominal cavity before the present invention, a special technology and method for implanting an external intra-pelvic fundus vesicae support are not used in surgical support implantation technology.

The present invention relates to the fields of the known medical tomoscan and three-dimensional data reconstruction technologies and three-dimensional print technology, and particularly to the manufacture of an individualized external intra-pelvic fundus vesicae support using the known printing technology of medical metal, ceramics and plastic material.

BACKGROUND

In modern traditional Chinese medicine, the understanding for the insufficiency of splenogastric qi generally stays in the principle of "man taking foodstuff as his major source of life" in "Neijing" which is based on the thought that "people are based on stomach qi" to illustrate the pathogenesis theory that "internal damage of the spleen and stomach causes all kinds of diseases" and initiate the therapeutical principles of invigorating the spleen and reducing yin fire. A systematic theoretical system for treatment based on syndrome differentiation for the case of internal injury of spleen and stomach is formed. Splenogastric qi defined in Spleen Gastric Theory from Li Dongyuan refers to the stage of qi of the spleen and stomach, and the stage of insufficiency of splenogastric qi caused by asthenia of splenogastric qi in physiological features from old age to death stage is not sufficiently recognized.

Using a treatment method by pulse addition and subtraction in the known Chinese ancient classical proved recipe "Recipe of Invigorating Spleen-Stomach and Replenishing Qi", qi of the latter heaven can be used to invigorate the consumed qi of the former heaven, so as to improve and retard the degree of lowering of internal organs for many years and delay the incurable stage. Age will eventually lead to insufficiency of splenogastric qi and asthenia of splenogastric qi of qi of the former heaven and will irreversibly result in lowering of the internal organs, which will seriously reduce the life quality of the old people to a helpless pain stage. Because the westernization conclusion is denied by modern traditional Chinese medicine theory in the verification research of splenogastric qi, a solution of using a method of implanting and decompressing the external intra-pelvic fundus vesicae support to recover the bladder position and eliminate the urological disorder in cluster of lesions is not used.

The known "Urinary Surgery" from Wu Jieping in physiological anatomy of western medicine has described "newborns have a higher bladder position than adults. The internal urethral orifice may reach the upper margin of pubic symphysis, and is generally positioned in the abdominal cavity. Even if the internal urethral orifice is at the top of the emptied bladder, the internal urethral orifice is still above the upper margin of pubic symphysis. With age, the bladder will gradually drop into the pelvis, reaching the human position around puberty . . . . The pelvic fascia and ligament formed by it around the bladder play a role of supporting the bladder and can maintain the bladder to be at a normal level." Only the objective law that the position of bladder moves down with age is found, and the acting force of this law is explained using fascia and laxity of ligament. it is not recognized that the objective law that the position of bladder moves down is caused by insufficiency of splenogastric qi in the body like classical traditional Chinese medicine, and it is also not recognized that the internal organs simultaneously drop with the age and treatment can only be conducted for the uropoiesis system. After prostate is excised, the functions still cannot be recovered. Autonomous functions are still replaced by inserting a catheter into urethra and bladder for manual micturition or using a support inside the urethra, which damages autonomous ecology step by step. Because western medical community does not correctly recognize the cluster of lesions in lowering of visceral organs in the abdominal cavity before the present invention, a method for implanting the external intra-pelvic fundus vesicae support is not used in surgical support implantation technology. The solution of recovering the bladder position for eliminating the disorder of the excretory system and remedying fascia and laxity of ligament is not used.

A technology for implanting a support inside the urethra in the medical record of the urinary system is closest to the present invention. The technology and the method directly implant a metal support into the urethra from an external orifice of urethra to expand the prostate and the urethra inside the internal and external physiological sphincter to achieve assisted micturition, and have the following defects: the functions of the prostate and the internal and external physiological sphincter are lost, strange feeling is obvious, infection is easy to appear, the cluster of lesions in the lowering of the visceral organs in the abdominal cavity cannot be eliminated, and the continuous deterioration of autonomous ecology cannot be improved. The technology of implanting the support into the urethra does not involve the abdominal surgical technology and method. The present invention implants the external intra-pelvic fundus vesicae support to lift the bladder, prevents the internal and external sphincter, the prostate and the urethra from being extruded, recovers the original physiological function, improves and recovers the autonomous ecological function of other organs, effectively eliminates the cluster of lesions and corrects the errors in the recognition of senile syndrome defined in western medical pathology.

The known technology of implanting the support into the body in western medicine is mature. However, there is no patented technology identical with or similar to the external intra-pelvic fundus vesicae support and the method for implanting same in the present invention.

The known technology of implanting the metal support into the urethra of the fundus vesicae completely loses the contraction and closure functions of the urethra and the urethra is open and is prone to infection. Occupying expansionary force enables male prostate to extrude the rectum and enables female urethra to directly extrude the rectum, which may cause difficult excretion of excrement and urine and proctoptosia. The technology of implanting the metal support into the urethra only plays the role of manually expanding the urethra to release urine.

The known virtual reality technology provides basic theory and basic hardware for the external intra-pelvic fundus vesicae support and the method for implanting same in the present invention to simulate and verify a bladder resetting surgical scheme through a virtual pelvic environment of the abdominal structural three-dimensional data of a typical person.

SUMMARY

The purpose of the present invention is to provide an external intra-pelvic fundus vesicae support and a method for implanting same to realize resetting for tenesmic organs in the abdominal cavity, eliminate extrusion injury of the organs in the pelvic cavity, recover the physiological functions of all internal organs of the body and substantively improve the life quality of middle-aged and elderly people and the lifetime.

According to the traditional Chinese medicine theory that insufficiency of splenogastric qi causes lowering of internal organs of the body, after research on an effective elimination method for cluster of lesions caused by mutual squeezing and damage of visceral organs in the pelvic cavity, the external intra-pelvic fundus vesicae support is invented. By an implantation method of disposing the rear end of the external intra-pelvic fundus vesicae support at the outer fundus vesicae position and fixing the front end to the pelvic pecten pubis position to lift a lowering body, squeezing and damage of visceral organs in the pelvic cavity below the urinary bladder are eliminated to realize functional recovery of the visceral organs. In the preparation of the external intra-pelvic fundus vesicae support, a known medical three-dimensional printing technical solution is used to convert abdominal tomoscan data into three-dimensional data; three-dimensional modeling software is used to change prototyping parameters of the external intra-pelvic fundus vesicae support to generate a model file of the external intra-pelvic fundus vesicae support which completely conforms to physiological shapes of the pelvic pecten pubis and the outer fundus vesicae and the spatial form of the abdominal cavity of a typical person, and an individualized external intra-pelvic fundus vesicae support entity of a frame structure and medical material quality is printed. An integral structure of the external intra-pelvic fundus vesicae support is formed by assembling a left and a right intra-pelvic fundus vesicae supports having the same mirror structure and a bridge, wherein the left and the right intra-pelvic fundus vesicae supports having the same mirror structure are provided with an upper pecten pubis hook, a screw hole, a bridge plate, a bridge plate pubic symphysis notch, bridge fixing holes, a bladder seat and a decompressing arc; the front end of the bridge plate is connected with the upper pecten pubis hook, and the rear end of the bridge plate is connected with the bladder seat; the bridge plate is disposed into a frame-shaped curved structure; the front end is provided with the pubic symphysis notch; the upper pecten pubis hook is arranged at the outer side of the notch; the curved surface of the upper pecten pubis hook is provided with an injection channel input hole and a screw hole; the bridge fixing holes are disposed at the inner side of the pubic symphysis notch; the bladder seat is disposed into a funnel shape that conforms to a bladder neck structure; the funnel-shaped central decompressing arc is disposed into a sphincter shape that avoids the bladder; an injection channel output hole is formed in an arc surface; an injection channel is arranged in a bridge plate section between the decompressing arc and the upper pecten pubis hook; a screw hole is arranged at the end of the injection channel input hole and used for disposing a sealing screw, an electrode or an in-vitro connector for delivering medicine; the bridge is disposed into an arch-shaped structure that conforms to the bridge plate curved surface; clamping heads with anti-fall structures are respectively arranged on planes of both ends of the cuboid; two clamping heads are matched and connected with two bridge fixing holes to fix the left and the right intra-pelvic fundus vesicae supports into a whole.

An integral structure of the external intra-pelvic fundus vesicae support is formed by assembling a left and a right intra-pelvic fundus vesicae supports having the same mirror structure and a bridge, wherein the front ends of the left and the right intra-pelvic fundus vesicae supports having the same mirror structure are connected with an upper pecten pubis hook; a screw hole is disposed in the curved surface; the upper pecten pubis hook is connected with the outer side of a front pubic symphysis notch of a bridge plate; the upper part of the upper pecten pubis hook is provided with an injection channel input hole; a screw hole is disposed in the injection channel input hole; the inner side of the front end of the bridge plate is connected with the pubis combining notch; bridge fixing holes are disposed in the bridge plate plane at the pubis combining notch; the rear end of the bridge plate is connected with a bladder seat; the bladder seat is disposed into a funnel shape that conforms to a bladder neck structure; a funnel-shaped central decompressing arc is disposed into a sphincter shape that avoids the bladder; an injection channel output hole is formed in an arc surface of the decompressing arc; the bridge plate is disposed into a frame-shaped curved structure; the injection channel output hole in the arc surface of the decompressing arc is connected to the injection channel input hole of the upper pecten pubis hook through an injection channel arranged in a bridge plate section; the screw hole arranged at the end of the injection channel input hole is used for connecting a sealing screw, an electrode or an in-vitro connector for delivering medicine; the bridge is disposed into an arch-shaped structure that conforms to the bridge plate curved surface; clamping heads with anti-fall structures are respectively connected to planes of both ends of the cuboid; and the left intra-pelvic fundus vesicae support is connected to one end of the bridge through a fixing hole, and the other end of the bridge is connected to the right intra-pelvic fundus vesicae support through the fixing hole, so as to connect into an entire external intra-pelvic fundus vesicae support.

A tomoscan device is used to collect abdominal data of a typical person; a medical three-dimensional printer is used to print the formed external intra-pelvic fundus vesicae support for standby.

The tomoscan device is used to collect abdominal data of a typical person before implanting. As described in known Wu Jieping Urinary Surgery that "newborns have a higher bladder position than adults. The internal urethral orifice may reach the upper margin of pubic symphysis, and is generally positioned in the abdominal cavity. Even if the internal urethral orifice is at the top of the emptied bladder, the internal urethral orifice is still above the upper margin of pubic symphysis. With age, the bladder will gradually drop into the pelvis, reaching the human position around puberty. Firstly, the abdominal tomoscan of the standing position of a human body is conducted to obtain three-dimensional spatial position data when the visceral organs completely drop; then the abdominal tomoscan of human supine declination position of 20 to 40 degrees is conducted to obtain three-dimensional spatial position data when no lowering of adult preadolescent organs is simulated, a three-dimensional database of the abdominal structure of the typical person is generated and converted into a three-dimensional modeling software data format, a file of an abdominal structural model of the typical person and an external intra-pelvic fundus vesicae support model after modifying prototyping parameters is created, and a bladder resetting surgical scheme is simulated and verified through a virtual pelvic environment of the abdominal structural three-dimensional data of the typical person and then is printed with a medical three-dimensional printer for standby; surgical operators practice through printouts of the abdominal structural model of the typical person and the fundus vesicae support model after modifying prototyping parameters to obtain all data of safe operation of the verified bladder resetting surgical scheme.

The implantation position of the external intra-pelvic fundus vesicae support is under pectineal ligament from the upper pecten pubis and the external side surface of the pecten pubis at the outer side of the pubic symphysis position to the outer bladder and external sphincter.

The implantation method is a surgical abdominal support implanting surgery; before a surgery is conducted according to the known abdominal surgical scheme, after aseptic treatment is completed, the liquid medicine is injected from the injection channel input hole; after no gas is discharged from the output hole, a special screw is used to seal the screw hole of the input hole to ensure that the postoperative liquid medicine can only exude from the injection channel output hole when conducting thermal expansion with the body temperature; operation is conducted according to the bladder resetting surgical scheme verified before the surgery to strip the tissue of the pectineal ligament and the upper pecten pubis without injury for reserving a gap for implanting the upper pecten pubis hook of the external intra-pelvic fundus vesicae support, so as to avoid the pubic symphysis position;

for men, the tissues between the outer fundus vesicae and the external sphincter and between the rear outer fundus vesicae and the ampulla of deferens duct are stripped without injury for reserving a gap for implanting the bladder seat of the rear end of the external intra-pelvic fundus vesicae support; for women, an atrophic womb is excised according to a known medical scheme; the vaginal orifice and the peritoneum are sutured to release the upper space of the bladder; non-injury stripping is conducted at the joint of the rear edge of the outer fundus vesicae and the outer wall of the vagina to create a gap; if stripping cannot be conducted, vaginal amputation is conducted to ensure that the bladder seat can be implanted into a required increased space; the opening at the vaginal amputation is sutured; when non-injury stripping is conducted at the joint among the front fundus vesicae, the pubis and the pecten pubis, clitoris tissue needs to be avoided to ensure that the left and the right intra-pelvic fundus vesicae supports, when connected and fixed in a non-contact state, do not press the clitoris tissue; the left and the right intra-pelvic fundus vesicae supports are inserted along the gap of the upper pecten pubis; the upper pecten pubis hook match the upper left pecten pubis, the upper right pecten pubis and the external side surface; the bladder seat and the outer fundus vesicae match and the internal sphincter is accurately avoided;

a medical electrical drill is used to position and drill according to the screw hole disposed in the curved surface of the upper pecten pubis hook; a medical screw is used to fix the external intra-pelvic fundus vesicae support to the external side surface of the pecten pubis to ensure that a screw cap does not protrude; clamping heads on both ends of the printed bridge are respectively pressed into a left and a right fixing holes of the bridge plate to ensure that the left and the right intra-pelvic fundus vesicae supports are connected and fixed in the non-contact state; and when implantation is completed, postoperative treatment is conducted according to the known abdominal surgical scheme.

An injection channel is arranged in a bridge plate section between the decompressing arc and the upper pecten pubis hook. When the injection channel is used as a drug release body, some liquid medicine can be stored; when the liquid medicine generates thermal expansion with the body temperature, the liquid medicine automatically exudes from the output hole; after internal pressure and external pressure of the injection channel are equal, the liquid medicine automatically stops exuding.

The screw hole is formed inside the injection channel input hole. After a connector is installed at the screw hole, the medicine can be injected in vitro directly into the outer fundus vesicae.

The screw hole is formed inside the injection channel input hole. After the in-vitro connector is installed at the screw hole, the connector can be used as an electrode for applying a physical method. The bladder resetting surgical scheme is simulated and verified through a virtual pelvic environment of the abdominal structural three-dimensional data of the typical person; a specific method is: a known virtual reality technology is used to build multiple Virtual Reality (VR) three-dimensional visual and tactile surgical instruments on an interaction platform of virtual operating table software and integrate into a surgery simulating engineering system; and the surgical operators exercise the bladder resetting surgical scheme in a virtual reality environment through the surgery simulating engineering system until a best method and a best effect are obtained.

The present invention has the following positive effects that:

The external intra-pelvic fundus vesicae support and the method for implanting same in the present invention can correct wrong disease recognition and treatment schemes in the field of senile diseases, correctly promote and develop the theoretical and practical achievements of the traditional Chinese medicine, reduce the waste of social medical resources and funds caused by mistakes and substantively improve the life quality and life confidence of middle-aged and elderly people.

When internal qi of the human body cannot be improved by medicine and causes deficiency of middle qi, or when quality of life of the middle-aged and elderly people is severely reduced due to excretory disorders to a helpless painful period, the external intra-pelvic fundus vesicae support and the method for implanting same in the present invention shall be used to eliminate cluster of lesions and substantively improve and enhance the life quality of the middle-aged and elderly people.

The external intra-pelvic fundus vesicae support and the method for implanting same of the present invention can lift the bladder to the upper pubic position to prevent the visceral organs in the abdominal cavity from lowering and recover the functions of the visceral organs.

The funnel-shaped central decompressing arc ensures relief of the pressure from the gravity on internal sphincter and external sphincter. Parasympathetic nerve recovers normal sensory and signal transmission functions without extruding prostate, urethra and rectum of man and urethra and rectum of women, so as to effectively alleviate or eliminate the cluster lesions of uropoiesis and related systems and recover the excretory function.

After the bladder is lifted to the upper pubic position, transverse colon and diaphragm are supported again and are prevented from further lowering so that cardiac and pulmonary functions are recovered and stabilized.

After the bladder is lifted to the upper pubic position, transverse colon is recovered to the original upper rear position through the newly supported upper part; jejunum and small intestine are recovered to their positions; and the peritoneum is decompressed, and hernia is eliminated. Extrusion pressure on the bladder is effectively reduced. The space above the bladder is increased. Urine storage quantity is gradually recovered to an original level.

After the bladder is lifted to the upper pubic position, pancreas and kidney eliminate downward pressure caused by the gravity to basically return to their positions through the new upper support; shapes and functions are recovered; and paroxysmal glycosuria and paroxysmal uremia gradually disappear.

After the bladder is lifted to the upper pubic position, gallbladder and liver eliminate downward force caused by the gravity to basically return to their positions through the new upper support; shapes and functions of gallbladder which is lengthened due to drop of the liver are recovered; unripe bile does not overflow; yellow urine and uremia symptoms disappear; cured bile recovers the digestion capability; and wet itching symptom of skin caused by acid body disappears.

After the bladder is lifted to the upper pubic position, upper visceral organs basically return to their positions. The top space of the bladder is recovered. The capacity when the bladder is full of urine is also increased and recovered. After the space in the trigonal region of the bladder is recovered, the internal pressure of the kidney will not be increased due to return of the urine. The bladder seat plays a role of supporting the bladder. The space released by the central decompressing arc allows the bladder and the external sphincter not to bear the weight when the bladder is extruded. Straining perception and nerve conduction control function are recovered. The symptoms of short urine, frequent micturition and urgent micturition disappear. Extruded force of seminal vesicle and seminal duct is eliminated, and the sexual function is recovered.

After the bladder is lifted to the upper pubic position, the lower prostate space is restored and the shape is recovered. Blood circulation is unimpeded. Stasis of blood and fluids are quickly metabolized completely. Inflammation and hypertrophy symptoms are eliminated. The internal passed urethra is recovered to be unblocked. The urinary retention symptom is eliminated. Micturition and defecation do not need additional force. The hernia symptom is eliminated. The functions of bulbourethral gland and ejaculatory duct are recovered. Ejaculatory pain type sexual dysfunction and restlessness caused by it are eliminated.

After the bladder is lifted to the upper pubic position, the lower urogenital diaphragm and other tissues recover their shapes and elasticity. The internal passed urethra and external rectum are not extruded. Urine and feces conduct retention and excretion alternately. Rectal hernia and ectropion of internal hemorrhoid are eliminated.

The frame structure of the external intra-pelvic fundus vesicae support has the following advantages: the adopted three-dimensional printing technology has low manufacturing cost, material saving, firmness, light weight, high coincidence accuracy and permeable structure capable of preventing infection and tissue gangrene caused by fluid retention in the contact position. The injection channel in the frame structure of the external intra-pelvic fundus vesicae support has the functions of delivering and storing the liquid medicine. After the connector is installed at the screw hole of the input hole, the medicine can be injected in vitro directly into the outer fundus vesicae. When the injection channel is used as a drug release body, some liquid medicine can be stored; and when the liquid medicine generates thermal expansion with the body temperature, the liquid medicine automatically exudes from the output hole for administration. After the connector is installed at the screw hole of the input hole, the connector can also be used as an electrode for applying a physical method.

The surgical operators use the surgery simulating engineering system integrated by the virtual reality technology to practice and verify the bladder resetting surgical scheme to ensure precision quality and safety of each surgery.

In the figures: 1 integral structure; 1-L wing support; 2 bladder seat; 3 decompressing arc; 4 injection channel output hole; 5 injection channel input hole; 5-1 inner venturi; 5-2 screw hole; 6 bridge; 6-1 arch-shaped structure; 6-2 clamping head; 7 bridge plate; 8 bridge fixing hole; 9 upper pecten pubis hook; and 10 screw hole.

DETAILED DESCRIPTION

Figure 1:
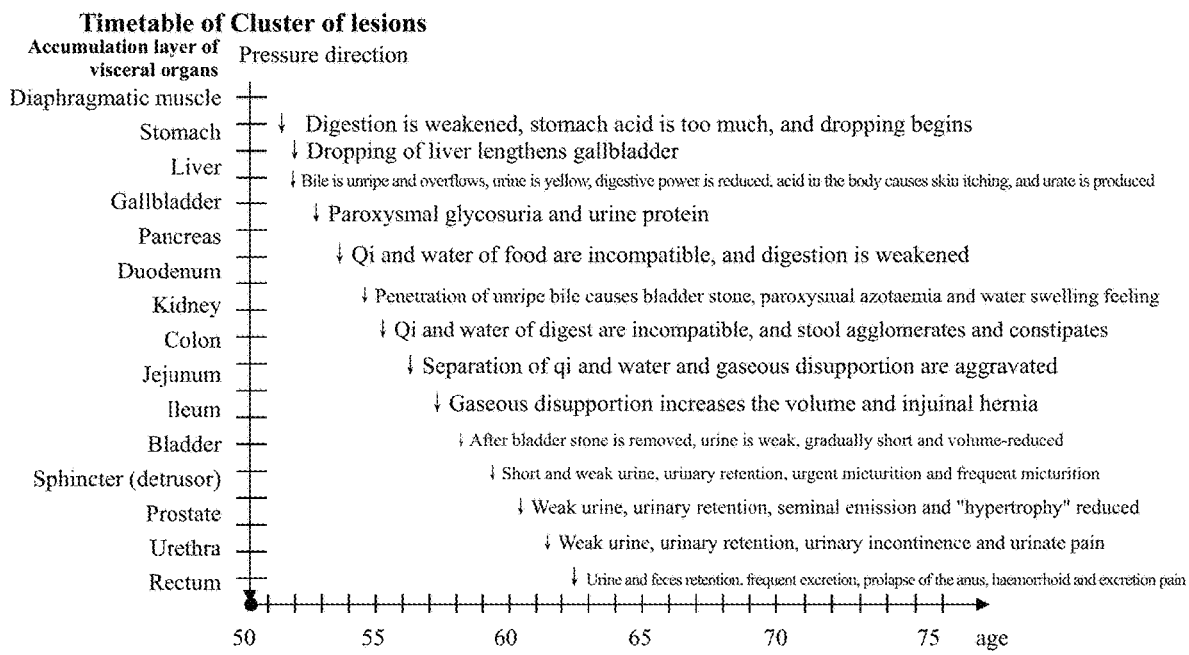
FIG. 1 is a schematic diagram of a timetable of cluster of lesions of the present invention.
Figure 2:
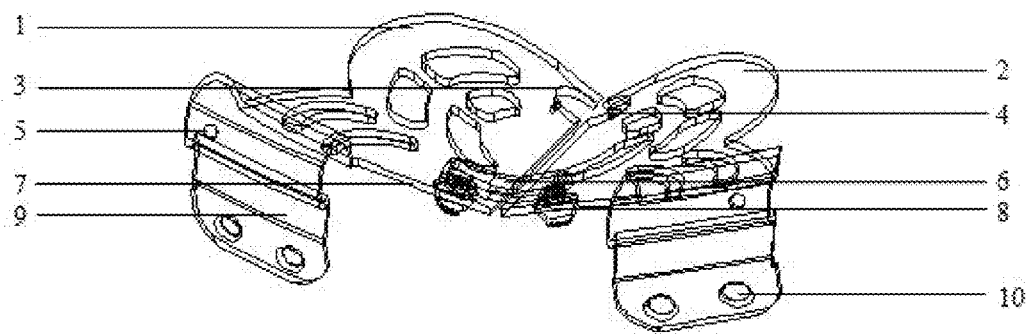
FIG. 2 is a three-dimensional structural schematic diagram of an assembly of an external intra-pelvic fundus vesicae support of the present invention.
Figure 3:
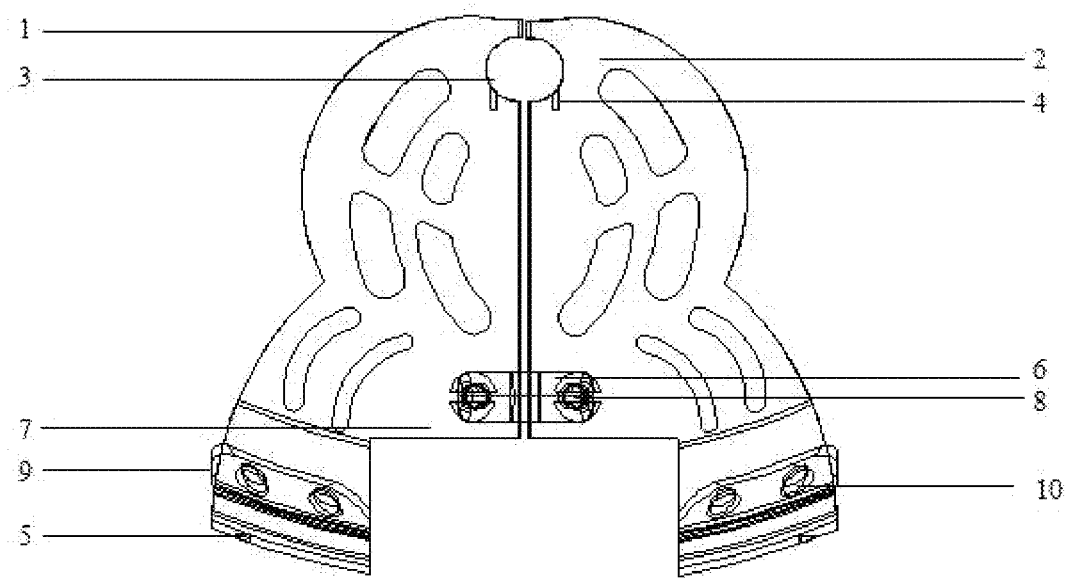
FIG. 3 is a top structural schematic diagram of an assembly of an external intra-pelvic fundus vesicae support of the present invention.
Figure 4:
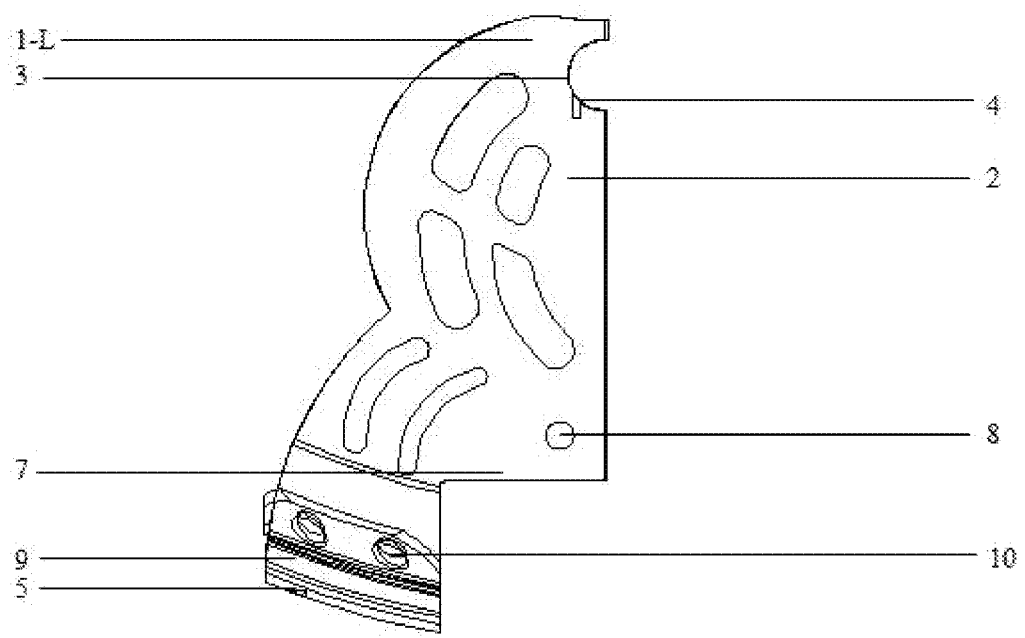
FIG. 4 is a top structural schematic diagram of a left intra-pelvic fundus vesicae support of the present invention.

As shown in FIG. 1, according to the timetable of the cluster of lesions, generally, when people reach the age of 50, the dropping of the organs has caused the decline of multiple organ functions, which influences the life quality. People born by caesarean section and people that have received abdominal surgery at an early age are earlier to generate more serious lowering of the organs than the time shown in the timetable of the cluster of lesion, and generally, the life quality is influenced before age of 50. People that take various sports and body building may suffer from the influence of the life quality after the age of 50. Women are generally later than men. When it is known that the visceral organs drop, pills for invigorating spleen-stomach and replenishing qi can be taken to alleviate lowering speed and degree. Validity is relevant to initial age and constitution when taking as well as taking method and dosage, and can maintain for 3 to 5 years. The known safe age for abdominal surgeries in western medicine is generally before the age of 60. It is suggested to use the external intra-pelvic fundus vesicae support and the method for implanting same in the present invention at the age of about 50, so as to avoid pain that may happen after the age of 50.

When the visceral organs in the abdominal cavity drop due to deficiency of qi in middle-jiao in the human body and the cluster of lesions occurs due to extrusion and damage in the pelvic cavity, the external intra-pelvic fundus vesicae support and the method for implanting same shall be used for elimination. As described in known Urinary Surgery from Wu Jieping that "newborns have a higher bladder position than adults. The internal urethral orifice may reach the upper margin of pubic symphysis, and is generally positioned in the abdominal cavity. Even if the internal urethral orifice is at the top of the emptied bladder, the internal urethral orifice is still above the upper margin of pubic symphysis. With age, the bladder will gradually drop into the pelvis, reaching the human position around puberty. The tomoscan device is used to collect abdominal data of a typical person before implanting. The data collection method of the external intra-pelvic fundus vesicae support comprises: firstly, conducting the abdominal tomoscan of the standing position of a human body to obtain three-dimensional spatial position data when the organs completely drop; then the abdominal tomoscan of human supine declination position of 20 to 40 degrees is conducted to obtain three-dimensional spatial position data when no lowering of adult preadolescent organs is simulated, a three-dimensional database of the abdominal structure of the typical person is generated and converted into a three-dimensional modeling software data format, a file of an abdominal structural model of the typical person and an external intra-pelvic fundus vesicae support model after modifying prototyping parameters is created, and a bladder resetting surgical scheme is simulated and verified through a virtual pelvic environment of the abdominal structural three-dimensional data of the typical person; the method is: a known virtual reality technology is used to build multiple VR three-dimensional visual and tactile surgical instruments on an interaction platform of virtual operating table software and integrate into a surgery simulating engineering system; and the surgical operators exercise the bladder resetting surgical scheme in a virtual reality environment through the surgery simulating engineering system until a best method and a best effect are obtained. After all safe operational data (including the three-dimensional spatial position data and the geometry data when the visceral organs completely drop, and the three-dimensional spatial position data and the geometry data of the visceral organs that can be lifted) of the verified bladder resetting surgical scheme is obtained, the safe operational data is converted into three-dimensional data of the modified support according to the three-dimensional spatial position data and the geometry data of the visceral organs that can be lifted; medical nanometer cermet material and preparation process are selected; and a medical three-dimensional printer is used to print the external intra-pelvic fundus vesicae support of the frame structure.

Parameters include intra-pelvic spatial position, pelvis and organ shape data. According to the abdominal structural data model of a typical person (including all the data of two groups of models in the lowering state and the lifted state), the bladder resetting surgical scheme is exercised in the virtual reality environment through the surgery simulating engineering system to obtain the verified safe operation data; and the prototyping parameters of the external intra-pelvic fundus vesicae support are modified to generate a virtual external intra-pelvic fundus vesicae support of the typical person. The virtual external intra-pelvic fundus vesicae support is taken into the surgery simulating engineering system environment to repeat the exercise of the bladder resetting surgical scheme in the virtual reality environment until implantation operation is successful. The virtual external intra-pelvic fundus vesicae support completely match with the virtual three-dimensional spatial position of the lifted organs to obtain a model file of the external intra-pelvic fundus vesicae support, i.e., the model data of the external intra-pelvic fundus vesicae support.

As shown in FIGS. 2, 3, 4, 5 and 6, an integral structure 1 of the external intra-pelvic fundus vesicae support is formed by assembling a left and a right 1-L intra-pelvic fundus vesicae supports having the same mirror structure and a bridge 6. An upper pecten pubis hook 9, a screw hole 10, a bridge plate 7, a bridge plate pubic symphysis notch, bridge fixing holes 8, a bladder seat 2 and a decompressing arc 3 are arranged in the external intra-pelvic fundus vesicae supports structure. The upper pecten pubis hook is a curved structure, and has a hooked section. One side of the curved surface is connected to the front end of the bridge plate, and the rear end of the bridge plate is connected to the bladder seat. The upper pecten pubis hook is arranged at the outer side of the bridge plate pubic symphysis notch; and the surface of the upper pecten pubis hook is provided with an injection channel input hole 5 and a screw hole 5-2. The bridge plate 7 is disposed into a reticular curved structure. The front end is provided with the pubic symphysis notch. The bridge fixing holes 8 are formed in the plane of the bridge plate at the pubic symphysis notch. The rear end is provided with the bladder seat 2. The bladder seat is disposed into a funnel shape that conforms to a bladder neck structure. A funnel-shaped central decompressing arc 3 is disposed into a sphincter shape that avoids the bladder. An injection channel output hole 4 is formed in an arc surface of the decompressing arc. An injection channel connecting input hole 5 and output hole 4 are formed in the section of the bridge plate.

The front ends of the left and the right intra-pelvic fundus vesicae supports having the same mirror structure are connected with an upper pecten pubis hook (used to buckle pecten pubis from the upper pecten pubis position); a screw hole (used to firmly position the external intra-pelvic fundus vesicae support and the pecten pubis) is disposed in the curved surface; the upper pecten pubis hook is connected with the outer side of a front pubic symphysis notch of the bridge plate; the upper part of the upper pecten pubis hook is provided with an injection channel input hole; a screw hole is disposed in the injection channel input hole; the inner side of the front end of the bridge plate is connected with the pubic symphysis notch; bridge fixing holes are disposed at the pubic symphysis notch; the rear end of the bridge plate is connected with a bladder seat; the bladder seat is disposed into a funnel shape that conforms to a bladder neck structure; a funnel-shaped central decompressing arc is disposed into a sphincter shape that avoids the bladder; an injection channel output hole is formed in an arc surface of the decompressing arc; the bridge plate is disposed into a frame-shaped curved structure; the injection channel output hole in the arc surface of the decompressing arc is connected to the injection channel input hole of the upper pecten pubis hook through an injection channel arranged in a bridge plate section; the screw hole arranged at the end of the injection channel input hole is used for connecting a sealing screw, an electrode or an in-vitro connector for delivering medicine; the bridge is disposed into an arch-shaped structure that conforms to the bridge plate curved surface; clamping heads with anti-fall structures are respectively connected to planes of both ends of the cuboid; the left intra-pelvic fundus vesicae support is connected to one end of the bridge through a fixing hole, and the other end of the bridge is connected to the right intra-pelvic fundus vesicae support through the fixing hole, so as to connect into an entire external intra-pelvic fundus vesicae support.

The upper pecten pubis hook, the bridge plate and the bladder seat in the left or the right intra-pelvic fundus vesicae support form an integral structure. The cuboid of the bridge and the clamping head form an arch-shaped structure, i.e., a doorframe type structure of a house. The lower plane of the cuboid matches the curved surface formed by connecting two bridge plates, and the upper plane is parallel to the lower plane. The angles formed by the upper plane and all the vertical planes are chamfered into circular arcs. Both ends of the lower plane of the cuboid are respectively connected with clamping heads with anti-fall structures. An angle formed by connecting the two bridge plates through the bridge is obtained according to an inherent symmetrical angle of the upper pecten pubis of the typical person.

Figure 5:
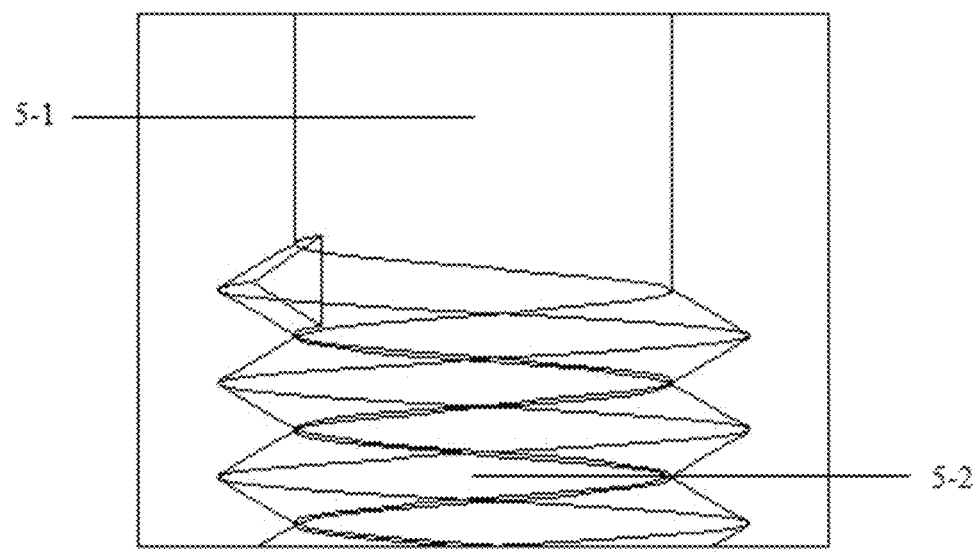
FIG. 5 is a local structural schematic diagram of a screw hole in an injection channel input hole of an external intra-pelvic fundus vesicae support of the present invention.

As shown in FIG. 5, an inner venturi 5-1 of the injection channel input hole formed in the surface of the upper pecten pubis hook is part of the injection channel, and has the same diameter as the injection channel. The screw hole 5-2 is connected outside the venturi and is used to arrange the electrode or the in-vitro connector for delivering medicine.

Figure 6:
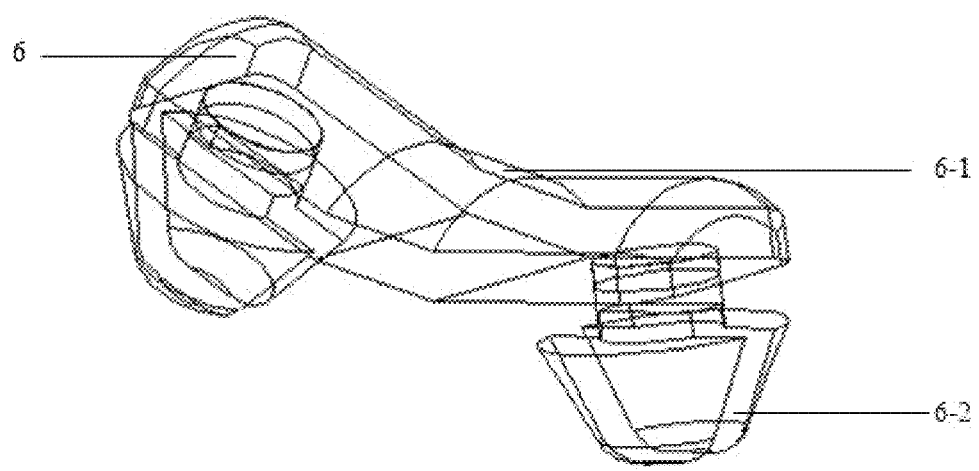
FIG. 6 is a structural schematic diagram of a bridge of an external intra-pelvic fundus vesicae support of the present invention.

As shown in FIG. 6, the bridge 6 is disposed into an arch-shaped structure 6-1 that conforms to the curved structure formed after combining the left and the right bridge plates. The arch-shaped structure 6-1 is printed using nylon plastic having the same elasticity and strength as pubic symphysis ligament. Planes of both ends of the cuboid above the arch-shaped structure are provided with clamping heads 6-2 with anti-fall structures. Two clamping heads are matched and fixedly connected with two bridge fixing holes into a whole to ensure that there is a fixed interval between left and right symmetrical edges of the external intra-pelvic fundus vesicae support.

The implantation method is a surgical abdominal support implanting surgery; before a surgery is conducted according to the known abdominal surgical scheme, after aseptic treatment is completed, the liquid medicine is injected from the injection channel input hole; after no gas is discharged from the output hole, a special screw is used to seal the screw hole of the input hole to ensure that the postoperative liquid medicine can only exude from the injection channel output hole when conducting thermal expansion with the body temperature; operation is conducted according to the bladder resetting surgical scheme verified before the surgery to strip the tissue of the pectineal ligament and the upper pecten pubis without injury for reserving a gap for implanting the upper pecten pubis hook of the external intra-pelvic fundus vesicae support, so as to avoid the pubic symphysis position;

for men, the tissues between the outer fundus vesicae and the external sphincter and between the rear outer fundus vesicae and the ampulla of deferens duct are stripped without injury for reserving a gap for implanting the bladder seat of the rear end of the external intra-pelvic fundus vesicae support; for women, an atrophic womb is excised according to a known medical scheme; the vaginal orifice and the peritoneum are sutured to release the upper space of the bladder; non-injury stripping is conducted at the joint of the rear edge of the outer fundus vesicae and the outer wall of the vagina to create a gap; if stripping cannot be conducted, vaginal amputation is conducted to ensure that the bladder seat can be implanted into a required increased space; the opening at the vaginal amputation is sutured;

when non-injury stripping is conducted at the joint among the front fundus vesicae, the pubis and the pecten pubis, clitoris tissue needs to be avoided to ensure that the left and the right intra-pelvic fundus vesicae supports, when connected and fixed in a non-contact state, do not press the clitoris tissue; the left and the right intra-pelvic fundus vesicae supports are inserted along the gap of the upper pecten pubis; the upper pecten pubis hook completely matches the upper left pecten pubis, the upper right pecten pubis and the external side surface; the bladder seat and the outer fundus vesicae match completely;

a medical electrical drill is used to position and drill according to the screw hole disposed in the curved surface of the upper pecten pubis hook; a medical countersink screw is used to fix the external intra-pelvic fundus vesicae support to the external side surface of the pecten pubis to ensure that a screw cap does not protrude; clamping heads on both ends of the printed bridge are respectively pressed into a left and a right fixing holes of the bridge plate to ensure that the left and the right intra-pelvic fundus vesicae supports are connected and fixed in the non-contact state; and when implantation is completed, postoperative treatment is conducted according to the known abdominal surgical scheme.

After a connector is installed at the screw hole of the injection channel input hole, the medicine can be injected in vitro directly into the outer fundus vesicae. When the injection channel is used as a drug release body, some liquid medicine can be stored; when the liquid medicine is completely injected, the connector is sealed to ensure that the liquid medicine can only exude from the output hole when the liquid medicine generates thermal expansion with the body temperature; and after internal pressure and external pressure of the injection channel are equal, the liquid medicine automatically stops exuding.

After the connector is installed at the screw hole of the injection channel input hole, the connector can be used as an electrode for applying a physical method.

The invention claimed is:

1. An external intra-pelvic fundus vesicae support, comprising:
    an integral structure of the external intra-pelvic fundus vesicae support formed by assembling a left and a right intra-pelvic fundus vesicae supports having the same mirror structure and a bridge,
    wherein the left and the right intra-pelvic fundus vesicae supports having the same mirror structure are provided with an upper pecten pubis hook, a first screw hole, a bridge plate, a bridge plate pubic symphysis notch, a plurality of bridge fixing holes, a bladder seat, and a decompressing arc;
    wherein the front end of the bridge plate is connected with the upper pecten pubis hook, and the rear end of the bridge plate is connected with the bladder seat;
    the bridge plate is disposed into a frame-shaped curved structure;
    the front end of the bridge plate is provided with the pubic symphysis notch;
    the upper pecten pubis hook is arranged at an outer side of the notch;
    a curved surface of the upper pecten pubis hook is provided with an input hole of an injection channel and a second screw hole;
    the plurality of bridge fixing holes are disposed at an inner side of the pubic symphysis notch;
    the bladder seat is disposed into a funnel shape that conforms to a bladder neck structure;
    a funnel-shaped central decompressing arc is disposed into a sphincter shape that avoids the bladder;
    an output hole of the injection channel is disposed in a surface of the funnel-shaped central decompressing arc;
    the injection channel is arranged in a bridge plate section between the decompressing arc and the upper pecten pubis hook;
    the second screw hole is arranged at an end of an injection channel input hole and used for disposing a sealing screw and a connector for delivering medicine;
    the bridge is disposed into an arch-shaped structure that conforms to a bridge plate curved surface;
    two clamping heads with anti-fall structures are respectively arranged on planes of both ends of a cuboid formed by the bridge and the two clamping heads; and
    the two clamping heads are matched and connected with two bridge fixing holes to fix the left and the right intra-pelvic fundus vesicae supports into a whole, and
    wherein front, left, right, and up are body relative directions.

2. The external intra-pelvic fundus vesicae support according to claim 1, wherein a tomoscan device is used to collect abdominal data of a typical person; a medical three-dimensional printer is used to print and form the external intra-pelvic fundus vesicae support.

3. The external intra-pelvic fundus vesicae support according to claim 1, wherein the injection channel is arranged in the bridge plate section between the injection channel output hole in an arc surface of the decompressing arc and the injection channel input hole in the upper pecten pubis hook; wherein the injection channel is configured to serve as a drug release body that stores a liquid medicine wherein the output hole is configured to allow the liquid medicine to exude; after internal pressure and pressure of the injection channel are equal, the liquid medicine automatically stops exuding; and
    the connector is installed at the second screw hole to form a path configured to allow the liquid medicine to be injected directly into the outer fundus vesicae.

4. An external intra-pelvic fundus vesicae support, comprising:
    an integral structure of the external intra-pelvic fundus vesicae support formed by assembling a left and a right intra-pelvic fundus vesicae supports having the same mirror structure and a bridge,
    wherein the front ends of the left and the right intra-pelvic fundus vesicae supports having the same mirror structure are connected with an upper pecten pubis hook;
    a first screw hole is disposed in a curved surface of the upper pecten pubis hook;
    the upper pecten pubis hook is connected with an outer side of a front pubic symphysis notch of a bridge plate;
    an upper part of the upper pecten pubis hook is provided with an input hole of the injection channel;
    a second screw hole is disposed in an injection channel input hole;
    an inner side of the front end of the bridge plate is connected with the pubic symphysis notch;
    a plurality of bridge fixing holes are disposed at the pubic symphysis notch;
    the rear end of the bridge plate is connected with a bladder seat;
    the bladder seat is disposed into a funnel shape that conforms to a bladder neck structure;
    a funnel-shaped central decompressing arc is disposed into a sphincter shape that avoids the bladder; an output hole of the injection channel is formed into an arc surface of the decompressing arc;
    the bridge plate is disposed into a frame-shaped curved structure;

an injection channel output hole in the arc surface of the decompressing arc is connected to the injection channel input hole of the upper pecten pubis hook through the injection channel arranged in a bridge plate section;

the second screw hole arranged at an end of the injection channel input hole is used for connecting a sealing screw and a connector for delivering medicine;

the bridge is disposed into an arch-shaped structure that conforms to a curved surface in the bridge plate;

two clamping heads with anti-fall structures are respectively connected to planes of two ends of a cuboid formed by the bridge and the two clamping heads;

the left intra-pelvic fundus vesicae support is connected to one end of the bridge through a fixing hole, and the other end of the bridge is connected to the right intra-pelvic fundus vesicae support through the fixing hole connectedly form the entire external intra-pelvic fundus vesicae support.

5. A method for implanting an external intra-pelvic fundus vesicae support, comprising:

conducting an abdominal tomoscan of the standing position of a patient to obtain three-dimensional spatial position data of a state in which the organs completely drop;

then conducting the abdominal tomoscan of the patient in a supine declination position of 20 to 40 degrees to obtain three-dimensional spatial position data of a state in which no lowering of adult preadolescent organs is simulated;

generating a three-dimensional database of abdominal structure of the patient;

converting the three-dimensional database into a three-dimensional modeling software data format;

creating a file of an abdominal structural model of the patient and an external intra-pelvic fundus vesicae support model after modifying prototyping parameters;

simulating and verifying a bladder resetting surgical scheme through a virtual pelvic environment of the three-dimensional data of abdominal structure of the patient and then printing with a medical three-dimensional printer for standby; and practicing by surgical operators through printouts of the abdominal structural model of the patient and the fundus vesicae support model after modifying prototyping parameters to obtain all data of safe operation of the verified bladder resetting surgical scheme, wherein the external intra-pelvic fundus vesicae support comprises an integral structure formed by assembling a left and a right intra-pelvic fundus vesicae supports having the same mirror structure and a bridge, wherein the left and the right intra-pelvic fundus vesicae supports having the same mirror structure are provided with an upper pecten pubis hook, a first screw hole, a bridge plate, a bridge plate pubic symphysis notch, a plurality of bridge fixing holes, a bladder seat, and a decompressing arc;

wherein the front end of the bridge plate is connected with the upper pecten pubis hook, and the rear end of the bridge plate is connected with the bladder seat;

the bridge plate is disposed into a frame-shaped curved structure;

the front end of the bridge plate is provided with the pubic symphysis notch;

the upper pecten pubis hook is arranged at an outer side of the notch;

a curved surface of the upper pecten pubis hook is provided with an input hole of the injection channel and a second screw hole;

the plurality of bridge fixing holes are disposed at an inner side of the pubic symphysis notch;

the bladder seat is disposed into a funnel shape that conforms to a bladder neck structure;

a funnel-shaped central decompressing arc is disposed into a sphincter shape that avoids the bladder;

an output hole of the injection channel is disposed in a surface of the funnel-shaped central decompressing arc;

the injection channel is arranged in a bridge plate section between the decompressing arc and the upper pecten pubis hook;

the second screw hole is arranged at the end of an injection channel input hole and used for disposing a sealing screw and a connector for delivering medicine;

the bridge is disposed into an arch-shaped structure that conforms to a bridge plate curved surface;

two clamping heads with anti-fall structures are respectively arranged on planes of both ends of a cuboid formed by the bridge and the two clamping heads; and the two clamping heads are matched and connected with two bridge fixing holes to fix the left and the right intra-pelvic fundus vesicae supports into a whole, and wherein front, left, right, and up are body relative directions.

6. The method for implanting the external intra-pelvic fundus vesicae support according to claim 5, wherein the external intra-pelvic fundus vesicae support is implanted in a cavity formed by pectineal ligament from the upper pecten pubis, a side surface of the pecten pubis at an outer side of the pubic symphysis position to the outer bladder and sphincter;

during operation on a male patient, tissues between the outer fundus vesicae and the sphincter and between the rear outer fundus vesicae and the ampulla of deferent duct are stripped without injury for reserving a gap for implanting the bladder seat of the rear end of the external intra-pelvic fundus vesicae support;

during operation on a female patient, an atrophic womb is excised; the vaginal orifice and the peritoneum are sutured to release the upper space of the bladder; non-injury stripping is conducted at the joint of the rear edge of the outer fundus vesicae and an outer wall of the vagina to create a gap; when stripping cannot be conducted, vaginal amputation is conducted to ensure that the bladder seat is implanted into a required increased space; the opening at the vaginal amputation is sutured; when non-injury stripping is conducted at the joint among the front fundus vesicae, the pubis and the pecten pubis, clitoris tissue needs to be avoided to ensure that the left and the right intra-pelvic fundus vesicae supports;

the left and the right intra-pelvic fundus vesicae supports are inserted along the gap of the upper pecten pubis; the upper pecten pubis hook matches the upper left pecten pubis, the upper right pecten pubis and an external side surface of the pecten pubis; the bladder seat and the outer fundus vesicae match and the internal sphincter is accurately avoided; a medical electrical drill is used to position and drill according to the first screw hole disposed in the curved surface of the upper pecten pubis hook; a medical screw is used to fix the external intra-pelvic fundus vesicae support to the external side surface of the pecten pubis to ensure that a screw cap does not protrude; clamping heads on both ends of the printed bridge are respectively pressed into a left and a right fixing holes of the bridge plate to ensure that the left and the right intra-pelvic fundus vesicae supports are connected and fixed in a non-contact state.

7. The method for implanting the external intra-pelvic fundus vesicae support according to claim 5, wherein the injection channel is configured to receive a liquid medicine; and the second screw hole is formed inside the injection channel input hole for receiving the connector through which the liquid medicine is injected in vitro directly into the outer fundus vesicae or for receiving an electrode.

* * * * *